(12) United States Patent
Warratz et al.

(10) Patent No.: US 9,885,694 B2
(45) Date of Patent: Feb. 6, 2018

(54) METHODS AND DEVICES FOR DETECTION OF THE CONCENTRATION OF AT LEAST ONE GASEOUS TARGET SUBSTANCE AND USE OF A GAS MONITORING DEVICE

(71) Applicant: MSA AUER GmbH, Berlin (DE)

(72) Inventors: Ralf Warratz, Hamburg (DE); Martin Weber, Meckenheim (DE)

(73) Assignee: MSA EUROPE GMBH, Jona (CH)

( * ) Notice: Subject to any disclaimer, the term of this patent is extended or adjusted under 35 U.S.C. 154(b) by 216 days.

(21) Appl. No.: 14/409,805

(22) PCT Filed: Mar. 15, 2013

(86) PCT No.: PCT/EP2013/055463
§ 371 (c)(1),
(2) Date: Dec. 19, 2014

(87) PCT Pub. No.: WO2014/000898
PCT Pub. Date: Jan. 3, 2014

(65) Prior Publication Data
US 2015/0316522 A1      Nov. 5, 2015

(30) Foreign Application Priority Data

Jun. 28, 2012   (DE) .................. 10 2012 211 215

(51) Int. Cl.
*G01N 33/00* (2006.01)

(52) U.S. Cl.
CPC ..... *G01N 33/0006* (2013.01); *G01N 33/0036* (2013.01); *G01N 33/0054* (2013.01)

(58) Field of Classification Search
USPC ............................................. 73/31.05, 31.06
See application file for complete search history.

(56) References Cited

U.S. PATENT DOCUMENTS

| 4,247,380 A | 1/1981 | McIntyre |
| 4,961,834 A * | 10/1990 | Kuhn ................. G01N 33/0054 204/412 |

(Continued)

FOREIGN PATENT DOCUMENTS

| CH | 686981 A5 | 8/1996 |
| DE | 3841622 A1 | 6/1990 |

(Continued)

*Primary Examiner* — Paul West
*Assistant Examiner* — Mark A Shabman
(74) *Attorney, Agent, or Firm* — Bartony & Associates, LLC

(57) ABSTRACT

The invention concerns a method for detection of the concentration of at least one gaseous target substance (10) in a gas or a gas mixture (20), especially air, wherein: a) a first measured value (11) of the concentration of the at least one gaseous target substance (10) is saved as the first measured value (11) in a predetermined way and then b) the at least one target substance (10) is kept away from the sensor (1) with a gas shielding device (2) for a predetermined period of time, so that the concentration of the at least one target substance (10) measured by the sensor changes, c) before the end of the shielding of the sensor (1), the magnitude of the measured concentration and/or the direction of the change in concentration of the gaseous target substance (10) as detected by the sensor (1) is saved as the second measured value (12), d) the sensor (1) is then exposed again to the gas (20) with the at least one gaseous target substance (10), while e) on the basis of the difference between the first measured value (11) and the second measured value (12), an actual concentration of the at least one gaseous target substance (10) in the gas (20) is determined by means of a calculator (30). The invention also concerns a gas monitoring device and a use of such a device.

20 Claims, 4 Drawing Sheets

(56) References Cited

U.S. PATENT DOCUMENTS

| | | | |
|---|---|---|---|
| 6,202,408 B1 | 3/2001 | Lepperhoff | |
| 2009/0126454 A1* | 5/2009 | Pratt | G01N 33/0059 73/1.02 |
| 2013/0133309 A1* | 5/2013 | Zimmerman | F02D 41/222 60/274 |

FOREIGN PATENT DOCUMENTS

| | | |
|---|---|---|
| DE | 4132034 A1 | 4/1993 |
| WO | WO1992010751 A1 | 6/1992 |
| WO | WO2001020313 A1 | 3/2001 |
| WO | WO2009146693 A2 | 12/2009 |
| WO | WO2014000898 | 1/2014 |

* cited by examiner

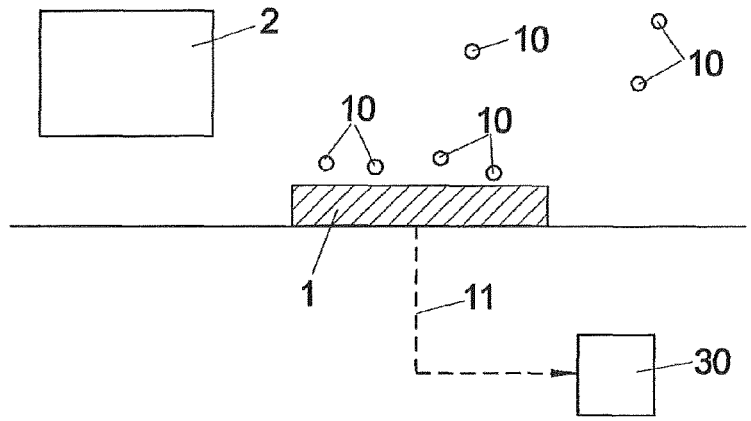
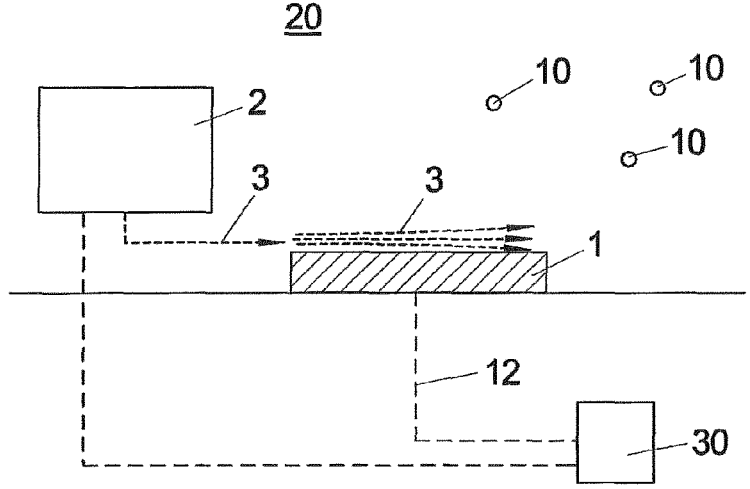
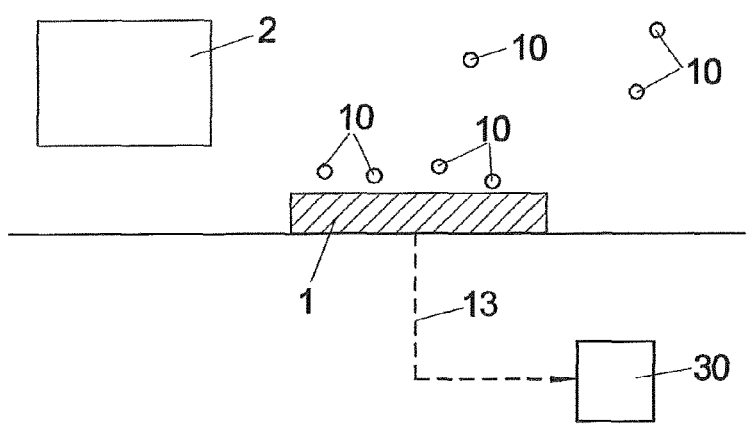

METHODS AND DEVICES FOR DETECTION OF THE CONCENTRATION OF AT LEAST ONE GASEOUS TARGET SUBSTANCE AND USE OF A GAS MONITORING DEVICE

CROSS-REFERENCE TO RELATED APPLICATION

This application is a US National Phase of PCT International Patent Application No PCT/EP2013/055463 filed Mar. 15, 2013 which claims the priority of German Patent Application No. 10 2012 211 215.4, filed Jun. 28, 2012, the disclosures of which are incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

The invention concerns methods and devices for detection of the concentration of at least one gaseous target substance in a gas, as well as the use of a gas monitoring or gas measurement device.

Detectors for gaseous target substances such as ammonia are basically familiar (CH 686981 A5, DE 3841622 A1). Electrochemical ammonia gas sensors are based, e.g., on the principle of direct oxidation of ammonia or measurement of the change in the pH value.

It has been observed that the performance of ammonia gas sensors slackens off upon long-term exposure, even at slight concentrations. For constant gas concentration, the measurement values of ammonia gas sensors tend toward zero over the course of time. This means that an ammonia-free environment is indicated, even though ammonia is present in the environment.

Therefore, the problem is to develop methods and devices which allow for the detection of a stable measurement of the gas concentration such as ammonia concentration in the surroundings over time.

SUMMARY

The problem set forth above is solved, for example, by the method with the features of claim 1. Methods and sensors hereof provide for the measurement of the concentration of the gaseous target substance in a gas or a gas mixture (especially, for example, air) In that regard, a method for detection of the concentration of at least one gaseous target substance in a gas includes: a) A first measured value of the concentration of the at least one gaseous target substance is saved as the first measured value (reference value) in a predetermined way.

b) The at least one target substance is then kept away from the sensor with a gas shielding device for a time so that the concentration of the at least one target substance measured by the sensor changes. The target substance can be shielded by a filter together with the gas or also selectively.

c) Before the end of the shielding of the sensor, the magnitude of the measured concentration and/or the direction of the change in concentration of the gaseous target substance as detected by the sensor is saved as the second measured value. d) The sensor is then exposed again to the gas with the at least one gaseous target substance.

e) On the basis of the difference between the first measured value and the second measured value, an output concentration of the at least one gaseous target substance in the gas is determined by using a calculator or processor.

Using the method hereof, it is possible to calibrate the sensor so that the observed saturation effect has no negative consequences. In addition to this calibration, one can also perform calibrations with test gases at greater distances. The term gas (or gas mixture) also includes a vapor (or vapor mixture).

In one advantageous embodiment, the gas shielding device includes a flushing device or system with which flushing of the sensor with a gaseous flushing medium (especially, for example, air) may be performed automatically or on demand. A user may, for example, perform the flushing on demand when he suspects that the measured values are no longer correct. In the case of the automatic control, one may set the duration of the flushing and defined intervals during which the flushing occurs.

In another example of an advantageous embodiment, flushing of the sensor is done with air from a pressurized gas bottle or gas supply. Pressurized air respirators with a pressurized gas bottle are, for example, regularly carried by fire fighters, and thus constitute an available source of the flushing gas for fire fighters.

Alternatively or additionally, another advantageous embodiment has a means of selective combustion of the gas, a mechanical gas barrier and/or filter device with which the target substance is kept away from the sensor for a predetermined time.

In one advantageous embodiment of the method, the time of shielding of the gas is more than 0.7 times the response time ($t_{90}$) of the sensor and less than 30 minutes. In another advantageous embodiment, the shielding of the gas with the target substance from the sensor is between 10 seconds and 5 minutes each time, especially between 20 seconds and 2 minutes or between 40 seconds and 2 minutes. In another advantageous embodiment, flushing with the gaseous flushing medium is done at intervals of 1 minute to 24 hours, especially every 5 to 30 minutes.

Advantageously, embodiments of the method can be used when the gaseous target substance is a nitrogen-containing gas, (especially, for example, ammonia, hydrazine or an amine) or a sulfur-containing gas (such as $H_2S$, a mercaptan, or thiophene).

In another embodiment, the problems set forth above are also solved by a device or sensor hereof. In that regard, a sensor (for example, an electrochemical sensor) outputs a measurement signal dependent upon a concentration of the gaseous target substance (that is, a first measured value as described above is determined). A gas shielding device temporarily shields the sensor from the gas. A calculator or processor determines an output concentration of the at least one target substance based upon a concentration measurement performed before shielding (first measured value) and another concentration measurement performed during shielding (second measured value). In theory, any given sensor can be used in this method.

In one advantageous embodiment of the sensor, the gas shielding device or system includes a flushing device for a flushing medium, wherein the flushing medium comes from a reservoir and/or from a gas generator. The reservoir may, for example, be a pressurized air reservoir, a pressurized or supplied air respirator and/or the surroundings from which the flushing medium is taken in.

Alternatively or additionally, one advantageous embodiment includes a means of selective combustion of the gas, a mechanical gas barrier and/or a filter device with which the gas is kept away from the sensor for a predetermined period of time.

It is advantageous for the sensor to have substantial inertia or be fairly insensitive to a change in relative humidity. This is especially beneficial because, for example, many electrochemical ammonia sensors exhibit a pronounced transient upon changes in relative humidity. That transient is then superimposed on all other changes. Such changes include the concentration change in question here, when, for example, the flushing medium for example has a relative humidity different from the surroundings being metered. This will especially be the case when the flushing gas comes from a pressurized gas bottle and is thus very dry.

It is also advantageous in a number of embodiments for the measurement principle of the sensor to be based on the principle of direct oxidation of ammonia or the measurement of changes in pH value. The latter as such is known, so that embodiments of the can be combined with this known feature.

In another aspect hereof, a method for detection of the concentration of at least one gaseous target substance in a gas with a sensor, includes a) measuring a first measured value of concentration of the at least one gaseous target substance in gas; b) subsequently shielding the at least one target substance from the sensor for a predetermined period of time, so that the concentration of the at least one target substance measured by the sensor changes, c) during shielding of the sensor, measuring a second measured value of concentration of the at least one gaseous target substance, d) after ceasing shielding of the sensor, exposing the sensor again to the gas with the at least one gaseous target substance, and e) determining an output concentration of the at least one gaseous target substance on the basis of the difference between the first measured value and the second measured value using a processor.

Shielding the sensor from the at least one target substance may, for example, include flushing of the sensor with a gaseous flushing medium. The gaseous flushing medium may, for example, include air. Flushing of the sensor may, for example, be initiated automatically or upon demand. In a number of embodiments, flushing of the sensor is done with air from a pressurized gas bottle or from a gas generator.

Shielding of sensor may, for example, include at least one of selective combustion of the gas, use of a protective electrode, use of a mechanical gas barrier or use of a filter device via which the at least one gaseous target substance is kept away from the sensor for a predetermined period of time. An protective electrode can mean that the gas shielding device might comprise an electrode that could function as a barrier when an oxidative process might be initiated with an appropriate applied electrical potential. Basically, this protective electrode would be able to oxidize $NH_3$ to avoid that the $NH_3$ gets to the sensing electrode of the NH3 sensor applied to the "gas shielding device". Removing the applied potential would allow the gas to diffuse through the protective electrode. In an advantageous embodiment, this protective electrode could actually be even installed in the $NH_3$ sensor itself on top of the sensing electrode; the alternative approach might be to have this protective electrode being installed in the separate "gas shielding device". Overall, this protective electrode should allow an alternative way to keep the target gas away from the sensor, other than the already mentioned combustion of the gas, the mechanical barriers and/or the filter device.

In a number of embodiments, the time of shielding of the gas is more than 0.7 times the length of a response time ($t_{90}$) of the sensor and less than 30 minutes. Shielding of the gas may, for example, be between 10 seconds and 5 minutes. In a number of embodiments, shielding of the gas lasts between 20 seconds and 2 minutes. Shielding of the gas may, for example, be done at intervals of 1 minutes to 24 hours. In a number of embodiments, shielding of the gas is done at intervals of 5 to 30 minutes.

Shielding may, for example, include flushing with a gaseous flushing medium. In a number of embodiments, the gaseous target substance is a nitrogen-containing gas. The gaseous target substance may, for example, be ammonia, hydrazine, an amine or a sulfur-containing substance.

In a further aspect, a device for the detection of the concentration of at least one gaseous target substance in a gas includes: (a) a sensor, which outputs a measurement signal dependent upon a concentration of the at least one gaseous target substance, (b) a gas shielding system for temporary shielding of the sensor from the gas, and (c) a processor to determine an output concentration of the at least one target substance based upon a concentration measurement performed before shielding and another concentration measurement performed during the shielding.

The gas shielding system may, for example, include a flushing device for delivering a flushing medium from a reservoir. The flushing medium may, for example, be delivered from a pressurized or supplied air respirator or taken in from the surroundings. In a number of embodiments, the gas shielding system includes a system for selective combustion of the at least one gaseous target substance, a mechanical gas barrier, or a filter device via which the at least one gaseous target substance is kept away from the sensor for a predetermined period of time.

In a number of embodiments, the response of the sensor exhibits substantial insensitivity to a rise in relative humidity. In a number of embodiments, the measurement principle of the sensor is based on direct oxidation of ammonia or the measurement of changes in pH value.

Advantageous uses of devices hereof include use in a stationary or in a portable gas detection system.

The present methods and devices, along with the attributes and attendant advantages thereof, will best be appreciated and understood in view of the following detailed description taken in conjunction with the accompanying drawings and representative embodiments.

BRIEF DESCRIPTION OF THE DRAWINGS

FIG. 1 illustrates a basic diagram of one embodiment of an ammonia gas sensor before a flushing.

FIG. 2 illustrates a basic diagram of the embodiment of FIG. 1 during a flushing with a gaseous flushing medium;

FIG. 3 illustrates a basic diagram of the embodiment of FIG. 1 after a flushing with a gaseous flushing medium;

DETAILED DESCRIPTION

Figure 4:
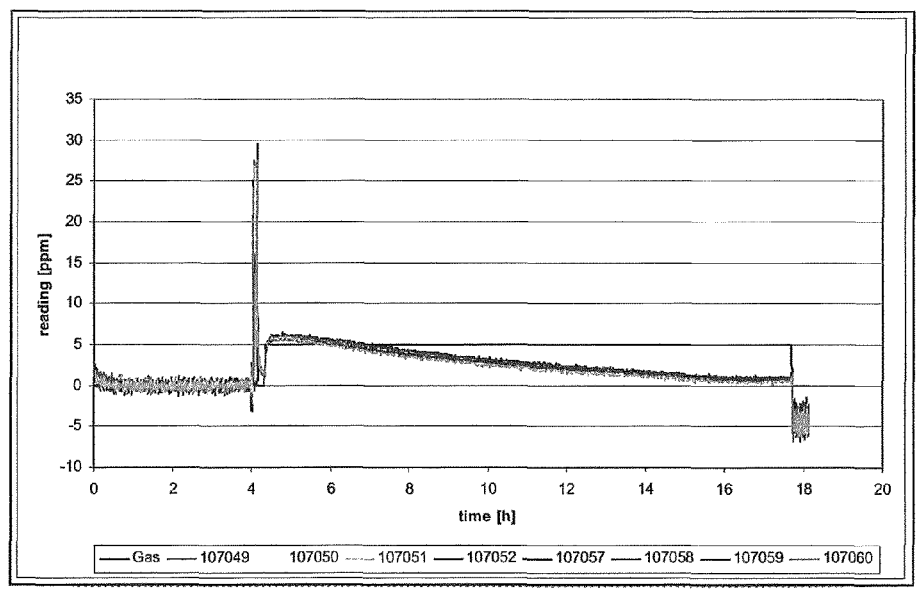
FIG. 4 illustrates a first concentration measurement of an amperometric $NH_3$ sensor with a flushing.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "shielding system" includes a plurality of such shielding systems and equivalents thereof known to those skilled in the art, and so forth, and reference to "the shielding system" is a reference to one or more such shielding systems and equivalents thereof known to those skilled in the art, and so forth.

FIG. 1 illustrates schematically a sensor 1 with which the concentration of at least one gaseous target substance 10 in a gas, here, air 20 (for example, the surrounding or ambient air), may be measured. Such a device may, for example, be part of a portable or stationary gas detector.

Basically, the design and functional principle of the sensor 1 will not be discussed hereafter; any sensor 1 may be used that can measure a concentration of the gaseous target substance 10 in the air 20.

The function of the devices described herein and the methods described herein are independent of the type of the at least one gaseous target substance 10. In what follows, we shall refer as an example to the measurement of the concentration of gaseous ammonia ($NH_3$) in air. In similar fashion, other gaseous target substances 10, preferably containing nitrogen, such as hydrazine or amines or sulfur-containing substances may also be measured by the sensor 1.

FIG. 1 illustrates that the concentration of the gaseous target substance 10 is detected by the sensor 1, and the measurement result is relayed to a calculation system or processor 30. The processor 30 may be, for example, a microchip, which is installed in a handheld device or a stationary device for gas monitoring.

After a while, the actual concentration of the at least one gaseous substance 10, ammonia in this case, can no longer be measured correctly, since a type of saturation of the sensor 1 has taken place. The measured value for the concentration of ammonia 10 by the sensor 1 drops, even though the concentration of ammonia 10 in the air 20, for example, has remained constant.

Before a flushing is performed, as one option for temporary shielding of the sensor 1, at a predetermined moment in time (for example, after a certain period of time interval has elapsed), a measurement of the concentration of the gaseous target substance 10 is performed (that is, with the saturated, or at least partly saturated, sensor 1). The measured concentration is saved by the processor 30 as the first measured value 11.

FIG. 2 illustrates the same configuration as FIG. 1, but wherein a flushing medium 3 is passed from a flushing device 2 across the sensor 1 for a certain time. The length of the gas flushing is on the order of the usual response time ($t_{90}$) of the sensor 1 for example, $2 \times t_{90}$. For $t_{90}=45$ s, this would be 1.5 minutes of calibration time. A possible upper bound for the length of the shielding, or here the gas flushing, is 30 minutes.

The flushing medium 3 may be, for example clean air, which is arranged in the form of a small pressurized container or gas generator in the gas detector itself. In addition or alternatively, however, the clean air can also come from a pressurized or supplied air respirator or be supplied to the gas detector across a line. The flushing medium 3 should be free of target substances 10 that are being measured by the sensor 1.

The flushing of the sensor 1 with the flushing medium 3 constitutes a calibration. Before the end of the flushing of the sensor 1, the magnitude of the measured concentration and/or the direction of the concentration change of the gaseous target substance 10 as detected by the sensor 1 is saved as the second measured value 12.

The second measured value 12 obtained on the basis of the flushing will lead, in the present case, to a drop in the measured value for ammonia 10. If the measured value for ammonia 10 has already dropped to zero on account of the saturation effect of the sensor 1, the second measured value 12 may be negative (see FIG. 4). This second measured value 12 is saved by the processor 30 and used as the measured value for the calculation of the actual background concentration of ammonia 10. The difference between the first measured value 11 and the second measured value 12 is a measure of the drift or false measurement of the sensor 1.

FIG. 3 shows the next step of the method, in which the sensor 1 is again exposed to air 20 with ammonia 10. Any change in the second measured value 12 with respect to the first measured value 11 provides a measure of the drift of the sensor 1.

FIG. 4 shows a first concentration measurement with one embodiment of one of the above-described devices. For the first four hours, the sensor 1 is exposed to pure air. At time t=4 h, a concentration of 25 ppm of ammonia 10 in air 20 is applied abruptly. The result of this measurement is used to calibrate the sensor 1 and provides the information on the sensitivity of the sensor (e.g., 100 nA/ppm $NH_3$). This sensitivity is then used afterwards to perform all further concentration calculations on the basis of the current values. The primary task of the sensor in amperometric design is always a current measurement.

Although the ammonia concentration is held constant at 5 ppm afterwards (t>4 h), the measured value at time t=18 h drops to nearly 0 ppm. This can be called a saturation effect.

After 18 h, the sensor 1 is flushed with a flushing medium 3 in the manner described above. It is clearly evident that now the measured value for ammonia 10 becomes a negative measured value, namely, −5 ppm. This value is only understandable in relation to the previously measured saturation value of 0 ppm.

According to the embodiment described in FIGS. 1 to 3, the first measured value 11 corresponds to the measured value at t=4 h, i.e., 5 ppm. The second measured value 12 at t=18 h, i.e. 0 ppm, corresponds to the drop of −5 ppm. The magnitude of the difference between the first measured value 11 and second measured value 12 corresponds to the actual $NH_3$ concentration present before the flushing, i.e., 5 ppm.

Figure 5:
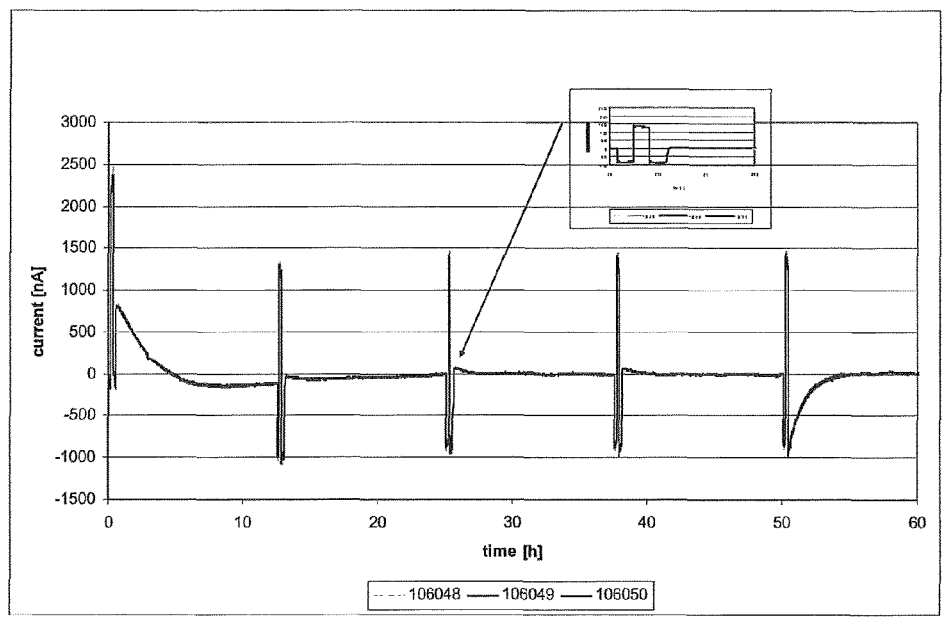
FIG. 5 illustrates a second concentration measurement with several flushings and concentration exposures of $NH_3$

FIG. 5 shows a second measurement series, in which a sensor 1 is exposed to air 20 with an ammonia concentration of 10 ppm. The concentration of 10 ppm $NH_3$ in this case simulates a possible background concentration of $NH_3$ and is interrupted by gas exposures of 25 ppm NH3 and flushing with clean air. The exposure of 25 ppm $NH_3$ and the flushing with air occurs at the start of the measurement series and also every 12 h. The measured value along the y axis is indicated here in nA, where 10 ppm corresponds to roughly 1000 nA.

It is clear that, like the measurement in FIG. 4, the sensor 1 after around 24 h shows a saturation effect. The measured value of the ammonia concentration has dropped from around 1000 nA to 0 nA (first measured value 11). By flushing with clear air at 12 h, a new baseline value is created for the sensor 1 by measuring a second measured value 12 of −1000 nA for the clean air (second measured value 12). When the sensor 1 is again exposed to air 20 with ammonia 10, the measured value again rises to 0 nA. The difference between the first measured value 11 (around 0 nA) and the second measured value (around −1000 nA) is the measure of the drift of the sensor 1.

The process is repeated several times afterwards. Within 50 h, four flushings with fresh air as the flushing medium and four verifications using 25 ppm of $NH_3$ are performed.

Figure 5A:
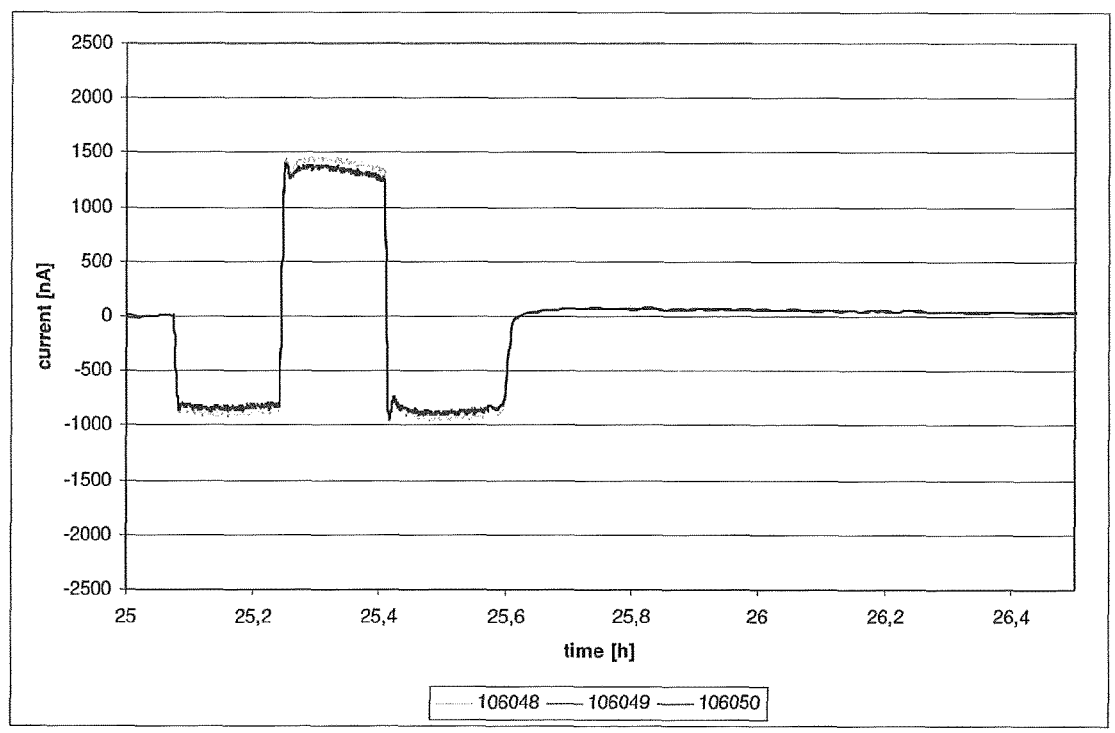
FIG. 5A illustrates a detail of flushings from the measurement per FIG. 5.

FIG. 5A presents a current measurement curve showing a small time segment (25 h and 26.5 h) of FIG. 5 at the same scale of the y axis. The events around the second flushing of the experimental series of FIG. 5 are presented in detail.

At the start (t=25-25.1 h), a current of 0 nA is measured, even though a concentration of 10 ppm of $NH_3$ (i.e., the target substance) is present in the surroundings. When the 10 ppm of $NH_3$ is removed from the sensor 1 (t=25.1 h), the measured current drops to nearly −1000 nA, i.e., an equivalent of −10 ppm of $NH_3$. When the target substance is again presented (around t=25.25 h) in a concentration of 25 ppm, the current value rises to around 1500 nA, corresponding to 15 ppm.

By means of the proposed method, the measured values can be corrected, namely, to 10 ppm of $NH_3$ in the region between t=25-25.1 h, 0 ppm in the region of t=25.1-25.25 h and 25 ppm in the region between t=25.1-25.4 h.

FIG. 5A also shows that the target substance is taken away again in the region of t=25.4-25.6, so that a current of around −1000 nA sets in. At t=25.6, the concentration of the target substance is again set at 10 ppm, so that once more 0 nA is measured. Corrected, the values are 0 ppm and 10 ppm.

Figure 6:
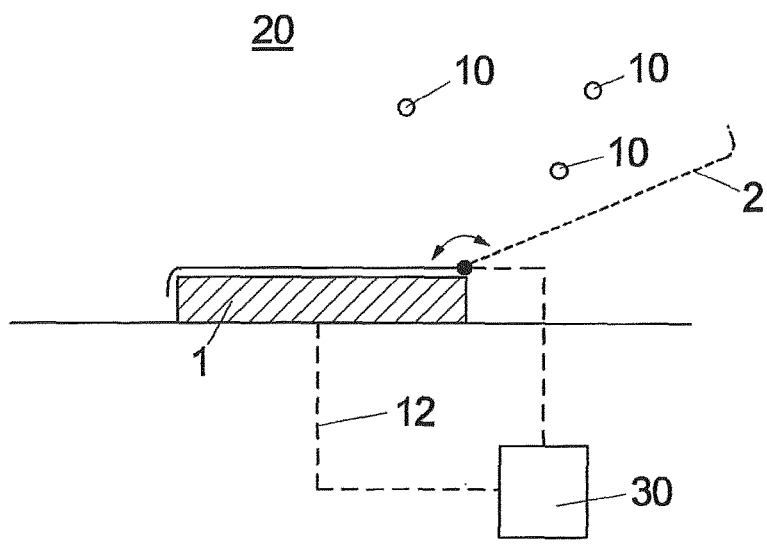
FIG. 6 illustrates another embodiment with a mechanical gas shielding.

FIG. 6 illustrates in schematic manner a mechanical gas shielding device 2 in which the sensor 1 can be shielded by a kind of lid from the at least one target substance 10. The lid-like arrangement here can be hinged on the sensor 1 by a flap mechanism. In other embodiments, the gas shielding device 2 can also be pushed across the sensor 1 or designed similar to a photographic diaphragm. Moreover, it is possible for a mechanical shielding to also have a filter that is specific for the target substance 10.

LIST OF REFERENCE SYMBOLS

1 sensor
2 flushing device/gas shielding device
3 flushing medium
10 gaseous target substance
11 first measured value (measured value before shielding/flushing)
12 second measured value
20 gas or gas mixture, especially air
30 calculator The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method for detection of the concentration of at least one gaseous target substance in a gas with a sensor, comprising:
   a) measuring a first measured value of concentration of the at least one gaseous target substance in the gas with the sensor;
   b) subsequently shielding the at least one target substance from the sensor for a predetermined period of time, so that the concentration of the at least one target substance measured by the sensor changes,
   c) during shielding of the sensor, measuring a second measured value of concentration of the at least one gaseous target substance with the sensor,
   d) after ceasing shielding of the sensor, exposing the sensor again to the gas with the at least one gaseous target substance, and
   e) determining an output concentration of the at least one gaseous target substance on the basis of the difference between the first measured value and the second measured value using a processor.

2. The method of claim 1 wherein shielding the sensor from the at least one target substance comprises flushing of the sensor with a gaseous flushing medium.

3. The method of claim 2 wherein the gaseous flushing medium comprises air.

4. The method of claim 2 wherein flushing of the sensor is initiated automatically or upon demand.

5. The method claim 2 wherein flushing of the sensor is done with air from a pressurized gas bottle or from a gas generator.

6. The method of claim 1 wherein shielding of sensor comprises at least one of selective combustion of the gas, use of a protective electrode, use of a mechanical gas barrier or use of a filter device via which the at least one gaseous target substance-is kept away from the sensor for a predetermined period of time.

7. The method of claim 1 wherein the time of shielding of the gas is more than 0.7 times the length of a response time (t90) of the sensor and less than 30 minutes.

8. The method of claim 1 wherein shielding of the gas lasts between 10 seconds and 5 minutes.

9. The method of claim 1 wherein shielding of the gas lasts between 20 seconds and 2 minutes.

10. The method of claim 1 wherein shielding of the gas is done at intervals of 1 minutes to 24 hours.

11. The method of claim 1 wherein shielding of the gas is done at intervals of 5 to 30 minutes.

12. The method of claim 1 wherein shielding comprises flushing with a gaseous flushing medium.

13. The method claim 1 wherein the gaseous target substance is a nitrogen-containing gas.

14. The method claim/wherein the gaseous target substance is ammonia, hydrazine, an amine or a sulfur-containing substance.

15. A device for detection of the concentration of at least one gaseous target substance in a gas comprising:
 (a) a sensor, which outputs a measurement signal dependent upon a concentration of the at least one gaseous target substance,
 (b) a gas shielding system for temporary shielding of the sensor from the gas, and
 (c) a processor configured to determine an output concentration of the at least one target substance based upon a concentration measurement performed with the sensor before shielding and another concentration measurement performed with the sensor during the shielding.

16. The device of claim 15 wherein the gas shielding system comprises a flushing device for delivering a flushing medium from a reservoir.

17. The device of claim 16 wherein the flushing medium is delivered from a pressurized air respirator of taken in from the surroundings.

18. The device of claim 15 wherein the gas shielding system comprises a system for selective combustion of the at least one gaseous target substance, a mechanical gas barrier or a filter device via which the at least one gaseous target substance is kept away from the sensor-for a predetermined period of time.

19. The device of claim 15 wherein a response of the sensor exhibits substantial insensitivity to a change in relative humidity.

20. The device of claim 15 wherein a measurement principle of the sensor is based on direct oxidation of ammonia or the measurement of changes in pH value.

* * * * *

UNITED STATES PATENT AND TRADEMARK OFFICE
CERTIFICATE OF CORRECTION

PATENT NO.       : 9,885,694 B2
APPLICATION NO.  : 14/409805
DATED            : February 6, 2018
INVENTOR(S)      : Ralf Warratz and Martin Weber Page 1 of 1

It is certified that error appears in the above-identified patent and that said Letters Patent is hereby corrected as shown below:

In the Drawings

Sheet 1, FIG 3, delete the reference numeral "13" and insert --11--

In the Specification

Column 3, Line 59, delete "NH3" and insert --$NH_3$--
Column 7, Line 16, delete "NH3" and insert --$NH_3$--

In the Claims

Claim 5, Column 8, Line 50, delete "The method claim 2" and insert --The method of claim 2--
Claim 6, Column 8, Line 57, delete "substance-is" and insert --substance is--
Claim 13, Column 9, Line 5, delete "The method claim 1" and insert --The method of claim 1--
Claim 14, Column 9, Line 7, delete "The method claim/" and insert --The method of claim 1--
Claim 18, Column 10, Line 11, delete "the sensor-for" and insert --the sensor for--

Signed and Sealed this
Seventeenth Day of July, 2018

Andrei Iancu
*Director of the United States Patent and Trademark Office*